United States Patent
Ma et al.

(10) Patent No.: US 9,549,961 B2
(45) Date of Patent: Jan. 24, 2017

(54) COMPOSITION FOR PREVENTING OR TREATING LIVER TOXICITY COMPRISING GALGEUNTANG OR LACTIC ACID BACTERIA FERMENTED GALGEUNTANG

(71) Applicant: Korea Institute of Oriental Medicine, Daejeon (KR)

(72) Inventors: Jin Yeul Ma, Daejeon (KR); Jae Hoon Lee, Daejeon (KR); Young Ran Um, Gyeongsangbuk-do (KR); Ji Hye Lee, Gyeongsangbuk-do (KR)

(73) Assignee: KOREA INSTITUTE OF ORIENTAL MEDICINE (KR)

(*) Notice: Subject to any disclaimer, the term of this patent is extended or adjusted under 35 U.S.C. 154(b) by 61 days.

(21) Appl. No.: 13/926,412

(22) Filed: Jun. 25, 2013

(65) Prior Publication Data

US 2013/0287761 A1 Oct. 31, 2013

Related U.S. Application Data

(62) Division of application No. 13/496,101, filed as application No. PCT/KR2009/005502 on Sep. 25, 2009.

(30) Foreign Application Priority Data

Sep. 18, 2009 (KR) ........................ 10-2009-0088617

(51) Int. Cl.
| | |
|---|---|
| *A61K 36/906* | (2006.01) |
| *A61P 1/16* | (2006.01) |
| *C12P 1/04* | (2006.01) |
| *A61K 36/9068* | (2006.01) |
| *A61K 35/745* | (2015.01) |
| *A61K 35/747* | (2015.01) |
| *A61K 36/488* | (2006.01) |
| *A61K 36/484* | (2006.01) |
| *A61K 36/54* | (2006.01) |
| *A61K 36/65* | (2006.01) |
| *A61K 36/725* | (2006.01) |

(52) U.S. Cl.
CPC ......... *A61K 36/9068* (2013.01); *A61K 35/745* (2013.01); *A61K 35/747* (2013.01); *A61K 36/484* (2013.01); *A61K 36/488* (2013.01); *A61K 36/54* (2013.01); *A61K 36/65* (2013.01); *A61K 36/725* (2013.01)

(58) Field of Classification Search
None
See application file for complete search history.

(56) References Cited

FOREIGN PATENT DOCUMENTS

| CN | 1273839 A | 11/2000 |
|---|---|---|
| CN | 1389220 A | 1/2003 |
| EP | 1 279 727 A1 | 1/2003 |
| KR | 10-0185619 B1 | 3/1999 |
| KR | 10-2000-0055832 A | 9/2000 |
| KR | 10-0319377 B1 | 1/2002 |
| KR | 10-2003-0080709 A | 10/2003 |
| KR | 10-2004-0078030 A | 9/2004 |
| KR | 10-2007-0066571 A | 6/2007 |
| KR | 10-0733335 B1 | 6/2007 |
| KR | 10-2009-0056383 A | 6/2009 |
| KR | 10-0918629 B1 | 9/2009 |

OTHER PUBLICATIONS

Lu et al. "Clinical observation of 60 cases of drug-induced liver injury treated with Cinnamomi ramulus and Ge Gen Tang (Kudzu decoction)", Shandong Journal of Traditional Chinese Medicine 26(4): 239-240, 2007, as translation by USPTO.*
Shen et al. "The protective effect of Zizyphus jujube fruit on carbon tetrachloride-induced hepatic injury in mice by anti-oxidative activities", Journal of Ethnopharmacology 122: 555-560, 2009.*
Kim et al. "Effect of herbal Ephedra sinica and Evodia rutaecarpa on body composition and resting metabolic rate: a randomized, double-blind clinical trial in Korean premenopausal women." Journal of Acupuncture and Meridian Studies 1 (2): 128-138, 2008.*
Warpole et al. "The weight of nations: an estimation of adult human biomass" BMC Public Health 12: 439-444, 2012.*
International Search Report for corresponding International Application No. PCT/KR2009/005502 (Form PCT/ISA/210) mailed Nov. 16, 2010.
Reddy et al., "Amylolytic bacterial lactic acid fermentation—A review", Biotechnology Advances 26:22-35, Jan. 2008.
KIPRIS machine translation of Korea 10-2003-0080709 A, Neung-Gi Lee, Oct. 2003.
KIPRIS machine translation of Korea 10-2007-0066571 A, Yeong-Cheol Lee, Jun. 2007.
Office Action from Chinese Patent Application No. 200980161522.7 (mailed Feb. 17, 2014).
Bo et al., "60 Clinical Observation Cases of Treating Drug-Induced Liver Injury (DILI) with Cinnamomi ramulus and Galgeuntang," *Shandong Journal of Traditional Chinese Medicine*, 26:4 (2007) (Abstract).

* cited by examiner

*Primary Examiner* — Emily Cordas
(74) *Attorney, Agent, or Firm* — Merchant & Gould P.C.

(57) ABSTRACT

The present invention relates to lactic acid fermented Galgeuntang, and a composition comprising the said lactic acid bacteria fermented Galgeuntang or Galgeuntang as an active ingredient, more particularly, to lactic acid fermented Galgeuntang prepared by the steps of inoculating lactic acid bacteria to Galgeuntang, culturing thereof, and fermenting thereof, and a composition for preventing or treating liver toxicity comprising the said fermented Galgeuntang or Galgeuntang. The composition of the present invention has treatment effect on liver toxicity, so that it can be effectively used as a liver function recovering agent or health food for liver function recovery.

6 Claims, 9 Drawing Sheets

US 9,549,961 B2

COMPOSITION FOR PREVENTING OR TREATING LIVER TOXICITY COMPRISING GALGEUNTANG OR LACTIC ACID BACTERIA FERMENTED GALGEUNTANG

This application is a divisional of U.S. patent application Ser. No. 13/496,101 filed 14 Mar. 2012, which is a U.S. National Stage Application under 35 U.S.C. §371 of International Patent Application No. PCT/KR2009/005502, filed 25 Sep. 2009, which claims the benefit of priority to Korean Patent Application No. 10-2009-0088617, filed 18 Sep. 2009, the disclosures of all of which are hereby incorporated by reference in their entireties. The International Application was published in Korean on 24 Mar. 2011 as WO 2011/034225.

TECHNICAL FIELD

The present invention relates to lactic acid bacteria fermented Galgeuntang, and a composition for preventing or treating liver toxicity comprising Galgeuntang or lactic acid bacteria fermented Galgeuntang.

BACKGROUND

Galgeuntang is a kind of oriental medicine prescription prepared by boiling down such herbs as galgeun (*Puerariae radix*), mahuang, ginger, jujube, licorice, peony, and gyeji (*Cinnamomi ramulus*), which has been prescribed for treating stiff-neck and waist, feeling chills, cold without sweating and with feeling like avoiding getting caught in wind, shivering with chills, fever, congestion, cold without sweating but with stiff-body and back, inflammation in eyes, ears, and nose, rash, and asthma, etc.

There are those methods to prepare valuable materials for human body by fermenting medicinal herbs after adding a microorganism for fermentation. For example, there is a method to create synergy effect in relieving intestinal disorders comprising the steps of co-culturing lactic acid bacteria having excellent growth rate and flavor with medicinal herb extract and fermenting the said mixture (Korean Patent No. 185619). There is another method to double the effect with maintaining the original characteristics of each raw material comprising the steps of fermenting the whole raw materials using fermented soybeans with selected grains and medicinal herbs by aging at low temperature (Korean Patent Publication No. 2004-0078030). However, there are no reports yet in relation to fermented Galgeuntang.

Thus, the present inventors performed the experiment, in which liver toxicity was induced in rats by treating carbon tetrachloride and then completed this invention by confirming that the liver toxicity could be treated by administering lactic acid bacteria fermented Galgeuntang or Galgeuntang itself.

SUMMARY OF THE INVENTION

Technical Problem

It is an object of the present invention to provide lactic acid bacteria fermented Galgeuntang, and a composition for preventing or treating liver toxicity comprising Galgeuntang or lactic acid bacteria fermented Galgeuntang as an active ingredient.

Technical Solution

The present invention provides lactic acid bacteria fermented Galgeuntang prepared by the steps of mixing medicinal herbs including Galgeun (*Puerariae radix*), Mahuang, Ginger, jujube, licorice, peony and gyeji (*Cinnamomi ramulus*), followed by hot water extraction leading to Galgeuntang; and fermenting the Galgeuntang by inoculating lactic acid bacteria thereto.

The said Galgeuntang is prepared by mixing 2-10 parts by weight of mahuang, 2-10 parts by weight of ginger, 2-10 parts by weight of jujube, 1-7 parts by weight of licorice, 1-7 parts by weight of peony, and 1-7 parts by weight of gyeji (*Cinnamomi ramulus*) with 12 parts by weight of Galgeun (*Puerariae radix*).

The lactic acid bacteria herein is preferably selected from the group consisting of *Bifidobacterium*, *Lactobacillus*, *Streptococcus*, *Leuconostoc*, *Pediococcus*, and *Lactococcus* sp. microorganisms, and particularly *Bifidobacterium* sp. microorganisms are more preferred.

The present invention also provides a method for the preparation of the said lactic acid bacteria fermented Galgeuntang comprising the following steps:

preparing Galgeuntang by hot water extraction of the mixture of medicinal herbs including Galgeun (*Puerariae radix*), mahuang, ginger, jujube, licorice, peony and gyeji (*Cinnamomi ramulus*);

inoculating the Galgeuntang prepared above with the culture solution of lactic acid bacteria mycelium; and inducing submerged fermentation with performing anaerobic culture of the Galgeuntang culture solution obtained above.

The above preparation method can preferably have an additional step of adjusting pH of the Galgeuntang to 6~8 before inoculating the culture solution of lactic acid bacteria mycelium and after preparing Galgeuntang.

The present invention also provides a composition for preventing or treating liver toxicity comprising at least one of those Galgeuntang and lactic acid bacteria fermented Galgeuntang as an active ingredient.

As described hereinbefore, Galgeuntang is prepared by hot water extraction of the mixture of medicinal herbs including Galgeun (*Puerariae radix*), mahuang, ginger, jujube, licorice, peony and gyeji (*Cinnamomi ramulus*), and the said lactic acid bacteria fermented Galgeuntang is also the lactic acid bacteria fermented composition prepared as described hereinbefore.

The said composition is to lower the activities of one or more enzymes selected from the group consisting of AST (aspartate aminotransferase), ALT (alanine aminotransferase), and LDH (lactate dehydrogenase).

The present invention further provides a health food for recovering liver function comprising at least one of those Galgeuntang and lactic acid bacteria fermented Galgeuntang as an active ingredient.

In a preferred embodiment of the present invention, rats were treated with carbon tetrachloride, which induces liver toxicity, and then administered with the conventional Galgeuntang and the lactic acid bacteria fermented Galgeuntang of the present invention. The conditions of the rats were observed.

As a result, no toxicity related symptoms were observed after the administration of the Galgeuntang or the lactic acid bacteria fermented Galgeuntang.

The present inventors measured the activities of AST, ALT, and LDH after the treatment of carbon tetrachloride by the said administration method. As a result, the inventors confirmed that the activities of the said enzymes, which were increased by the treatment of carbon tetrachloride, were decreased by the administration of the lactic acid bacteria fermented Galgeuntang. The above result indicated that the lactic acid bacteria fermented Galgeuntang of the present invention had treatment effect on liver toxicity.

The composition of the present invention contains lactic acid bacteria fermented Galgeuntang as an active ingredient. The said lactic acid bacteria fermented Galgeuntang can be administered orally and be used in general forms of pharmaceutical formulation. Solid formulations for oral administration are tablets, hard or soft capsules, liquids, and suspensions, etc. The pharmaceutical formulation can be prepared by using the pharmaceutically acceptable carriers, for example, excipients, binders, disintegrating agents, lubricants, solubilizers, suspending agents, preserving agents, or extenders.

The effective dose of lactic acid bacteria fermented Galgeuntang can be determined according to the condition of patient, age, gender, and complications, etc. In general, the dose is 1~40 ml per 1 kg/day for adult, and preferably 10~30 ml per 1 kg/day. It is preferred that each individual preparation contains one day dose or ½, ⅓ or ¼ of an individual dose of the lactic acid fermented Galgeuntang. Administration frequency is preferably 1~6 times a day. If long term administration is required, the dose can be lower than the above but higher dose can be accepted as well since the lactic acid fermented Galgeuntang has been proved to be very safe.

In addition, the present invention provides a health food for recovering liver function comprising the said composition.

The lactic acid fermented Galgeuntang of the present invention can be used as a food additive. In that case, the lactic acid fermented Galgeuntang can be added as it is or as mixed with other food components according to the conventional method. The mixing ratio of active ingredients can be regulated according to the purpose of use (prevention, health enhancement or treatment). In general, to produce health food or beverages, lactic acid fermented Galgeuntang is added preferably by 5~30 wt % and more preferably by 10~20 wt %. However, if long term administration is required for health and hygiene or regulating health condition, the content can be lower than the above but higher content can be accepted as well since the lactic acid fermented Galgeuntang has been proved to be very safe. And the kind of food herein is not limited.

Advantageous Effect

The composition of the present invention has treatment effect on liver toxicity, so that it can be effectively used as a liver function recovering agent or health food for liver function recovery.

MARK EXPLANATION

Figure 1:
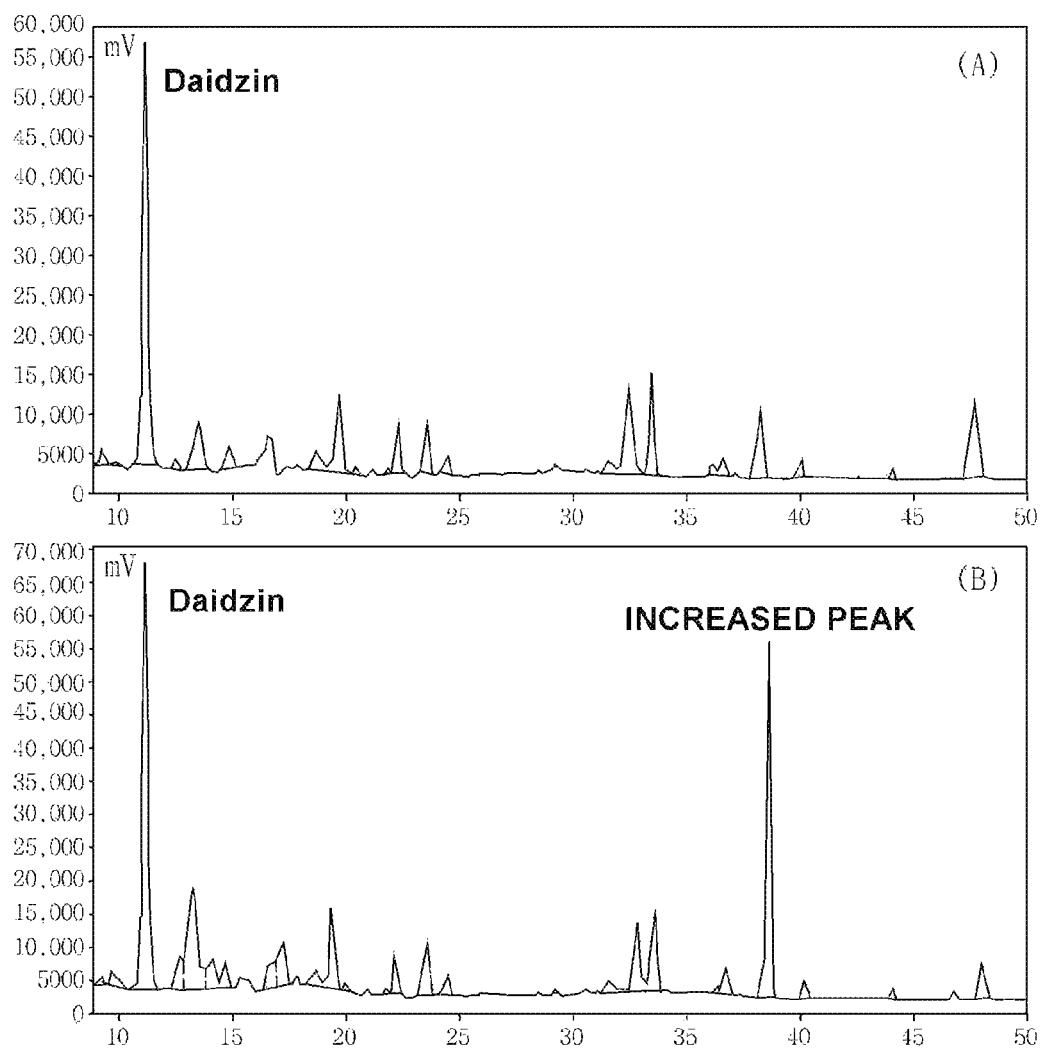
FIG. 1 (A) is a chromatogram of Galgeuntang, and FIG. 1 (B) is a chromatogram of lactic acid bacteria fermented Galgeuntang.

CV: central vein
N: centrilobular necrosis
← (arrow): vacuolar degeneration
▲ (arrow head): inflammatory cells infiltration

DETAILED DESCRIPTION

Practical and presently preferred embodiments of the present invention are illustrative as shown in the following Examples.

However, it will be appreciated that those skilled in the art, on consideration of this disclosure, may make modifications and improvements within the spirit and scope of the present invention.

Preparative Example 1

Preparation of Galgeuntang

Galgeuntang was prepared by hot water extraction of 120 g of Galgeun, 60 g of mahuang, 60 g of ginger, 60 g of jujube, 40 g of licorice, 40 g of peony, and 40 g of gyeji (*Cinnamomi ramulus*).

Example 1

Preparation of Lactic Acid Bacteria Fermented Galgeuntang

<1-1> Lactic Acid Bacteria

*Bifidobacterium breve* (KFRI 744, ATCC 15700) was obtained from KFRI (Korea Food Research Institute) and used for the following experiments.

<1-2> Seed Culture of Lactic Acid Bacteria

The distributed strain was sub-cultured in slant medium and liquid medium. First, the lactic acid bacteria were inoculated in slant medium, followed by culture in a 37° C. incubator for 24 hours. When colonies were formed, oxygen supply was blocked by using paraffin film, which was stored in a refrigerator. To avoid losing the activity of the bacteria or contamination by other microorganisms, the medium was replaced with fresh slant agar medium every 2~3 weeks. The colonies were inoculated in liquid medium, followed by culture in a 37° C. incubator for 24 hours.

RCM (Reinforced Clostridial Medium: 10 g/L Bacto-tryptose, 10 g/L Bacto-beef extract, 3 g/L Bacto-yeast extract, 5 g/L Bacto-dextrose, 5 g/L Sodium chloride, 1 g/L Soluble starch, 0.5 g/L L-cystein hydrochloride, 3 g/L Sodium acetate, 0.5 g/L Bacto-agar, pH 7.6) or Gam broth medium was used for the seed culture.

<1-3> Submerged Fermentation of Galgeuntang Using Lactic Acid Bacteria pH of the Galgeuntang prepared in Example 1 was adjusted to 7.0 with 1 M NaOH, followed by autoclaving at 1.5 atm, 121° C., for 15 minutes. After cooling to room temperature, the Galgeuntang was inoculated with lactic acid bacteria. The Galgeuntang was cultured anaerobically in a 37° C. incubator for 48 hours, leading to submerged fermentation. At this time, inoculum volume was 1% (v/v). After 48 hours of fermentation, pH changes were investigated.

When vegetables and grains were fermented by using Bifidobacteria, it was frequently observed that the proliferation of bacteria was inhibited, particularly in the fermentation of tomato, because of low pH. However, when pH was adjusted to 7.2, the population of bacteria was increased. In this example, pH of Galgeuntang was as low as 4.9 when it was not regulated. So, the inventors increased the pH by using 1 M NaOH solution for the fermentation. When pH of Galgeuntang was adjusted to 7.0 with 1 M NaOH solution before sterilization, the control pH was lowered from 7.0 to 5.9 before fermentation. This was presumably attributed that when Galgeuntang was sterilized at high temperature with high pressure (121° C., 1.5 atm, 15 minutes), some dietary fibers included in Galgeuntang were decomposed to organic acids with reducing pH. KFRI 744 (*B. breve*) was inoculated in the pH adjusted Galgeuntang and then cultured for 48 hours. Then, pH change was observed. As a result, pH of Galgeuntang was lowered to 4.3 by the fermentation, indicating active acid production.

<1-4> Analysis of Fermentation Product

1) Preparation of sample for HPLC

Residue of the fermented Galgeuntang was eliminated by centrifugation, followed by filtering with 0.45 μm filter. Then, HPLC was performed.

2) Analysis of metabolites by HPLC

To analyze changes of the materials metabolized by lactic acid bacteria before and after the fermentation of Galgeuntang, HPLC was performed, followed by comparative analysis of ingredients before and after the fermentation.

Analysis of metabolites of the fermented Galgeuntang by HPLC was performed according to the following conditions.

Operating Conditions of HPLC System for the Analysis of Fermented Products of Galgeuntang Column: reverse-phase column ($C_{18}$, 250×4.6 mm, 5 μm)
Detector: UV 254 nm
Solvent: A; water, B; acetonitrille
Run time: 70 minutes
Injection volume: 20 μl
Flow rate: 1.0 ml/min
Column temperature: 30° C.
Concentration gradients are shown in Table 1.

TABLE 1

| Time (minute) | A/B |
| --- | --- |
| 0 | 85/15 |
| 10 | 85/15 |
| 50 | 65/35 |
| 55 | 20/80 |
| 58 | 20/80 |
| 63 | 80/20 |
| 70 | 85/15 |

As a result, as shown in FIG. 1, from the result of comparing the lactic acid bacteria fermented Galgeuntang (FIG. 1 (B)) and the non-fermented Galgeuntang (FIG. 1(A)), it was confirmed that the peak at the time point of 38.2 min was increased as much as 6.4 times by the fermentation. Daidzin (24.3 min), one of the representative index materials of Galgeuntang, was detected in every sample.

Experimental Example 1

Treatment Effect on Liver Toxicity

<1-1> Test Animals

Male rats at 8 weeks were obtained from Orient Co. Ltd. (459-24, Gasan-dong, Geumcheon-gu, Seoul), which were then quarantined and acclimated in an animal lab of KIOM (Korea Institute of Oriental Medicine) for 2 weeks. Then, healthy animals were selected for the experiment.

<1-2> Determination of Dosage

To investigate the liver protective effect of the Galgeuntang prepared by traditional oriental medicine prescription and the lactic acid bacteria fermented Galgeuntang of the present invention, rats were treated with carbon tetrachloride ($CCl_4$) for 24 hours, and then damage of liver was examined. Administration dosage of Galgeuntang was determined as 15 ml/kg based on daily intake (3 times, 3 packs) and dosage of the fermented Galgeuntang was determined as 7.5, 15, and 30 ml/kg.

<1-3> Animal Grouping and Identification

Animal grouping was performed as follows. First, those rats selected as healthy during acclimation were weighed. Animals were grouped according to the weight range of every 5 g and those animals whose weights were close to the average weight were selected, 60 rats each. Then, those 60 rats were sub-grouped by 10 animals per group according to the weight ranks and random numbers (see Table 2). Hair/skin staining and individual identification card were used for the identification of each rat.

TABLE 2

| Group | Sex | Animal Number | $CCl_4$ (ml/kg) | Volume (ml/kg) | Dose (ml/kg) |
| --- | --- | --- | --- | --- | --- |
| CON | male | 1~10 | 0 | 30 | 0 |
| NCT | male | 11~20 | 1.0 | 30 | 0 |
| GGT | male | 21~30 | 1.0 | 30 | 15 |
| $GFT_1$ | male | 31~40 | 1.0 | 30 | 7.5 |
| $GFT_2$ | male | 41~50 | 1.0 | 30 | 15 |
| $GFT_3$ | male | 51~60 | 1.0 | 30 | 30 |

CON: control group
NCT: negative control group
GGT: group administered Galgeuntang (15 ml/kg)
$GFT_1$; group administered Galgeuntang fermented with *Bifidobacterium breve* (7.5 ml/kg)
$GFT_2$; group administered Galgeuntang fermented with *Bifidobacterium breve* (15 ml/kg)
$GFT_3$; group administered Galgeuntang fermented with *Bifidobacterium breve* (30 ml/kg)

<1-4> Statistical Method

In this experiment, statistical significances between the negative control and the experimental group treated with the test materials were calculated with means and standard deviations obtained by Dunnett test (*$p<0.05$, **$p<0.01$).

<1-5> Treatment and Prevention Effect on Liver Toxicity

Carbon tetrachloride ($CCl_4$) is one of the most representative liver toxicity inducing materials, which has been widely used for the studies on liver toxicity. The mechanism causing liver toxicity of carbon tetrachloride is known as follows. Carbon tetrachloride is metabolized to form $CCl_3$ and Cl free radicals in liver. These free radicals are working with unsaturated fatty acid in cell membrane to induce lipid peroxidation.

To evaluate the liver protective effect of Galgeuntang and lactic acid bacteria fermented Galgeuntang, Galgeuntang or lactic acid bacteria fermented Galgeuntang was administered to rats (experimental group) 30 minutes before liver toxicity was induced.

Carbon tetrachloride (1.0 ml/kg) was administered to SD male rats by intraperitoneal injection to induce liver toxicity. Blood was drawn 24 hours later, and then activities of AST, ALT, and LDH were measured respectively. Liver was weighed after drawing blood and complete blood count was performed. Liver tissue morphology was also observed.

As a result, death was not observed in any experimental group (see Table 3), and any toxicity symptom was not detected according to the administration of Galgeuntang and lactic acid bacteria fermented Galgeuntang (see Table 4).

TABLE 3

Summary report on death rate
Limit test male
Number of dead animal
Time after administration

| Group | Dose (ml/kg) | Number of dead animal/ Number of animal | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|---|---|
| CON | 0 | 0/10 | — | — | — | — | — | — | — | — | — | — | — | — | — | — | — | — | — | — | — | — | — | — | — | — |
| NCT | 0 | 0/10 | — | — | — | — | — | — | — | — | — | — | — | — | — | — | — | — | — | — | — | — | — | — | — | — |
| GGT | 15 | 0/10 | — | — | — | — | — | — | — | — | — | — | — | — | — | — | — | — | — | — | — | — | — | — | — | — |
| $GFT_1$ | 15 | 0/10 | — | — | — | — | — | — | — | — | — | — | — | — | — | — | — | — | — | — | — | — | — | — | — | — |
| $GFT_2$ | 15 | 0/10 | — | — | — | — | — | — | — | — | — | — | — | — | — | — | — | — | — | — | — | — | — | — | — | — |
| $GFT_3$ | 15 | 0/10 | — | — | — | — | — | — | — | — | — | — | — | — | — | — | — | — | — | — | — | — | — | — | — | — |

CON: control group
NCT: negative control group
GGT: group administered Galgeuntang (15 ml/kg)
$GFT_1$; group administered Galgeuntang fermented with *Bifidobacterium breve* (7.5 ml/kg)
$GFT_2$; group administered Galgeuntang fermented with *Bifidobacterium breve* (15 ml/kg)
$GFT_3$; group administered Galgeuntang fermented with *Bifidobacterium breve* (30 ml/kg)

TABLE 4

Clinical symptom of male rats by $CCl_4$ administration

| Variable | \Sex | Male | | | | | |
|---|---|---|---|---|---|---|---|
| | \Group | CON | NCT | GGT | $GFT_1$ | $GFT_2$ | $GFT_3$ |
| | \$CCl_4$(ml/kg) | 0 | 1.0 | 1.0 | 1.0 | 1.0 | 1.0 |
| | \Dose(ml/kg) | 0 | 0 | 15 | 7.5 | 15 | 30 |
| | \Number of animal | 10 | 10 | 10 | 10 | 10 | 10 |
| Normal | | 5 | 5 | 5 | 5 | 5 | 5 |
| Abnormal | | 0 | 0 | 0 | 0 | 0 | 0 |

CON: control group
NCT: negative control group
GGT: group administered Galgeuntang (15 ml/kg)
$GFT_1$; group administered Galgeuntang fermented with *Bifidobacterium breve* (7.5 ml/kg)
$GFT_2$; group administered Galgeuntang fermented with *Bifidobacterium breve* (15 ml/kg)
$GFT_3$; group administered Galgeuntang fermented with *Bifidobacterium breve* (30 ml/kg)

<1-6> Complete Blood Count

Hematologic examination was performed with EDTA-2K treated WBC, RBC, HGB, HCT, and PLT using JT Counter (Coulter Co., Miami, USA).

SD rats, the test animals, were fasted for 16 hours, which were then administered orally with the test materials, Galgeuntang (15 ml/kg) or lactic acid fermented Galgeuntang (7.5, 15 and 30 ml/kg). 30 minutes after the administration of test materials, carbon tetrachloride was intraperitoneally injected once (1.0 ml/kg/day). 24 hours later, blood was drawn and analyzed. As a result, no abnormal changes by those test materials were detected in blood cells. The decrease of red blood cell number in $GFT_2$ group and the increase of platelet number in $GFT_3$ group were all in the normal variation range, which were regarded not induced by those test materials (see Table 5).

TABLE 5

Hematological value of Galgeuntang and fermented Galgeuntang

| Test | WBC | RBC | HGB | HCT | MCV | MCH | MCHC | PLT |
|---|---|---|---|---|---|---|---|---|
| Unit | ×1000 | ×$10^6$ | g/dl | % | fl | pg | g/dl | ×1000 |
| Group: CON (control group) | | | | | | | | |
| Mean | 6.58 | 6.76 | 12.95 | 42.75 | 63.25 | 19.15 | 30.30 | 1023.33 |
| SD | 1.46 | 0.30 | 0.54 | 2.01 | 1.56 | 0.41 | 0.25 | 205.78 |
| Group: NCT (negative control group) | | | | | | | | |
| Mean | 6.96 | 7.29 | 13.98 | 46.40 | 63.66 | 19.19 | 30.13 | 838.75 |
| SD | 1.15 | 0.67 | 1.16 | 3.82 | 1.16 | 0.33 | 0.15 | 156.06 |
| Group: GGT (group administered Galgeuntang: 15 ml/kg) | | | | | | | | |
| Mean | 7.24 | 7.36 | 13.80 | 45.28 | 61.58 | 18.74 | 30.44 | 898.00 |
| SD | 1.82 | 0.18 | 0.53 | 1.41 | 3.18 | 1.04 | 0.40 | 191.62 |
| Group: $GFT_1$ (group administered fermented Galgeuntang: 7.5 ml/kg) | | | | | | | | |
| Mean | 9.21 | 7.13 | 13.40 | 45.54 | 63.94 | 18.77 | 29.40 | 792.86 |
| SD | 2.63 | 0.46 | 1.67 | 2.25 | 2.16 | 1.80 | 3.00 | 157.66 |
| Group: $GFT_2$ (group administered fermented Galgeuntang: 15 ml/kg) | | | | | | | | |
| Mean | 8.34 | 6.29* | 13.52 | 41.34 | 65.62 | 22.14 | 33.74 | 946.00 |
| SD | 3.38 | 1.23 | 1.22 | 8.11 | 0.40 | 4.69 | 7.34 | 272.54 |
| Group: $GFT_3$ (group administered fermented Galgeuntang: 30 ml/kg) | | | | | | | | |
| Mean | 8.12 | 6.92 | 13.40 | 43.74 | 63.24 | 19.36 | 30.68 | 1130.00* |
| SD | 2.17 | 0.59 | 0.94 | 3.50 | 1.18 | 0.65 | 0.59 | 268.70 |

Statistical significances were calculated for the negative control (*$p < 0.05$, **$p < 0.01$).
Dose of 15 ml/kg is one day dose of Galgeuntang for adult (3 bottles/60 kg/day).

<1-7> Biochemical Examination of Blood

Liver damage was induced with carbon tetrachloride, and then Galgeuntang (15 ml/kg) and fermented Galgeuntang (7.5, 15 and 30 ml/kg), the test materials, were orally administered to the test animals. 30 minutes after the administration of test materials, carbon tetrachloride was intraperitoneally injected once (1.0 ml/kg/day). 24 hours later, liver function damage was evaluated.

For biochemical examination of blood, 5 and of blood was drawn from caudal vena cava. The blood was coagulated at room temperature, followed by centrifugation at 5000 rpm for 10 minutes using refrigerated high speed centrifuge (Avanti 30, Beckman Co., USA). The levels of AST, ALT, and LDH were measured by using biochemical analyzer (Advia 1650, Shimaz Co., Japan).

Figure 2:
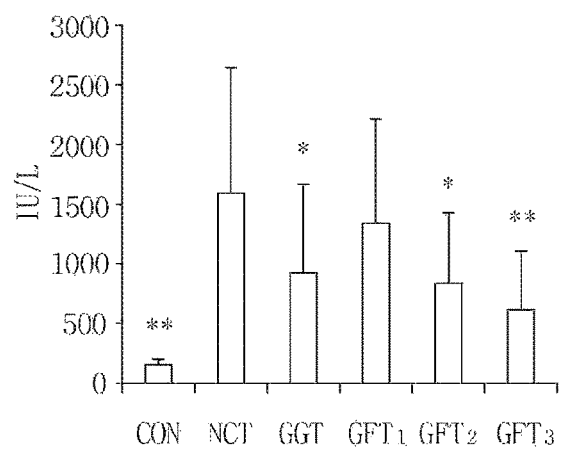
FIG. 2 is a set of graphs illustrating the results of biochemical examination of blood performed in Experimental Example <1-7>.
Figure 2:
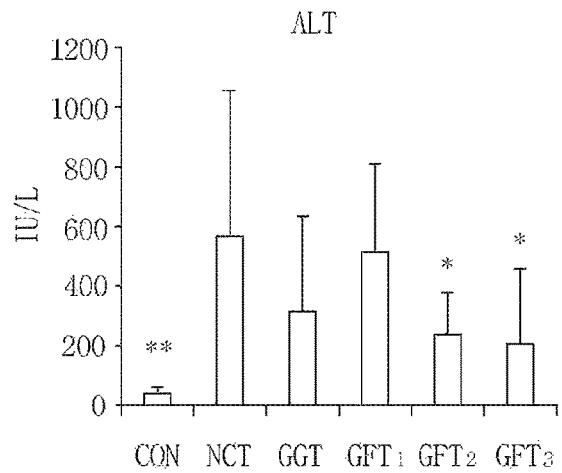
Figure 2:
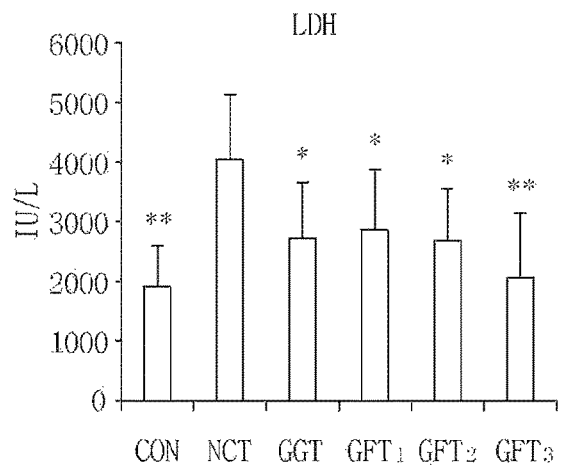

The results of the measurement were shown in Table 6 and FIG. 2. AST activity of the negative control group was measured as 1648.0 IU/L, which was 940.6% increased, compared with that of the normal control group (175.2 IU/L). AST activity was decreased 57.6% in GGT group, 81.9% in $GFT_1$ group, 51.9% in $GFT_2$ group, and 37.5% in $GFT_3$ group respectively, compared with that of the negative control group. When the SD rat was treated with carbon tetrachloride, AST content in serum was approximately 9.4 times increased. When the SD rat treated with carbon tetrachloride was administered orally with Galgeuntang or fermented Galgeuntang (Bifidobacterium breve), the level was decreased by the administration of fermented Galgeuntang dose dependently. Statistic significant difference was observed in the groups of GGT ($p<0.05$), $GFT_1$ ($p<0.05$), and $GFT_2$ ($p<0.05$).

ALT level of the negative control group was 583.11 IU/L, which was 1,554.9% increased, compared with that of the normal control group (37.5 IU/L). However, after the treatment of carbon tetrachloride followed by the administration of Galgeuntang and lactic acid bacteria fermented Galgeuntang, ALT level was decreased 54.8% in GGT group, 90.6% in $GFT_1$ group, 41.9% in $GFT_2$ group, and 35.4% in $GFT_3$ group respectively, compared with that of the negative control group. Statistic significant difference was also observed in $GFT_2$ group ($p<0.05$) and $GFT_3$ group ($p<0.05$).

LDH level in serum was 2.04 times increased in the group administered with Galgeuntang or lactic acid fermented Galgeuntang after the treatment of carbon tetrachloride, compared with that of the normal control group. When the test animal treated with carbon tetrachloride was administered orally with lactic acid bacteria fermented Galgeuntang, serum LDH level was decreased 69.1% in GGT group, 74.6% in $GFT_1$ group, 71.3% in $GFT_2$ group, and 54.6% in $GFT_3$ group respectively, compared with that of the negative control group. Statistic significant difference was also observed in the groups of GGT ($p<0.05$), $GFT_1$ ($p<0.05$), $GFT_2$ ($p<0.05$), and $GFT_3$ ($p<0.01$).

TABLE 6

Value of blood biochemistry of Galgeuntang and fermented Galgeuntang

| Variable | Sex | Male | | | | | |
|---|---|---|---|---|---|---|---|
| | Group | CON | NCT | GGT | $GFT_1$ | $GFT_2$ | $GFT_3$ |
| | Number of animal | 10 | 10 | 10 | 10 | 10 | 10 |
| AST; GOT (IU/L) | | $175.20^{a**}$ | 1648.00 | 949.60* | 1351.11 | 856.80* | 619.11** |
| | | $(20.39)^b$ | (1033.27) | (737.35) | (884.30) | (603.10) | (511.70) |
| ALT; GPT (IU/L) | | 37.50** | 583.11 | 319.80 | 528.67 | 244.80* | 206.56* |
| | | (4.81) | (488.61) | (326.68) | (293.82) | (137.31) | (252.04) |
| LDH (IU/L) | | 1903.00** | 3882.22 | 2684.80* | 2900.00* | 2769.00* | 2122.22** |
| | | (663.11) | (1500.95) | (1029.15) | (1031.41) | (898.73) | (797.81) |

CON: control group

NCT: negative control group

GGT: group administered Galgeuntang (15 ml/kg)

$GFT_1$; group administered Galgeuntang fermented with Bifidobacterium breve (7.5 ml/kg)

$GFT_2$; group administered Galgeuntang fermented with Bifidobacterium breve (15 ml/kg)

$GFT_3$; group administered Galgeuntang fermented with Bifidobacterium breve (30 ml/kg)

Statistical significances were calculated for the negative control (*$p < 0.05$, **$p < 0.01$).

$^a$Values are represented by mean.

$^b$±SD

<1-8> Liver Weight and Histologic Findings

After bleeding completely, livers of the test animals (SD rats, male) were weighed. The center part of the liver intermediate lobe was trimmed, followed by fixation in 10% neutral formalin solution. H&E staining was performed and then the tissues were observed morphologically.

Figure 3:
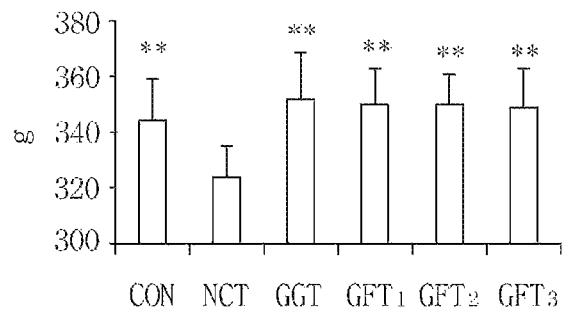
FIG. 3 is a set of graphs illustrating the results of liver weight measurement performed in Experimental Example <1-8>.
Figure 3:
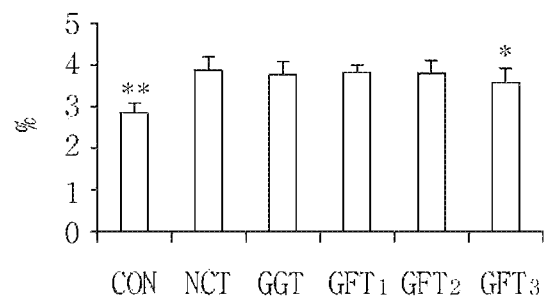

Particularly, liver damage was induced by treating carbon tetrachloride. Body weight was measured on the performance of autopsy. After bleeding completely, liver was extracted and weighed. The results are shown in Table 7 and FIG. 3. The weight was significantly reduced by the treatment of carbon tetrachloride. However, when Galgeuntang or fermented Galgeuntang was administered, the weight was significantly increased compared with NCT group ($p<0.01$).

The liver weight was converted to weight %. From the calculation was confirmed that the weight was significantly increased ($p<0.01$) in the group treated with carbon tetrachloride, compared with the control group, but decreased by the oral-administration of fermented Galgeuntang (30 ml/kg) ($p<0.05$).

TABLE 7

| Variable | Sex | | | | Male | | |
|---|---|---|---|---|---|---|---|
| | Group | CON | NCT | GGT | GFT$_1$ | GFT$_2$ | GFT$_3$ |
| | Number of animal | 10 | 10 | 10 | 10 | 10 | 10 |
| Body weight (g) | | 346.02$^a$** (16.08)$^b$ | 323.66 (12.09) | 354.46** (15.93) | 352.10** (13.30) | 351.68** (11.49) | 351.30** (14.80) |
| Weight change of liver (%) | | 2.91** (0.21) | 4.00 (0.27) | 3.85 (0.34) | 3.91 (0.16) | 3.89 (0.32) | 3.70* (0.35) |

CON: control group
NCT: negative control group
GGT: group administered Galgeuntang (15 ml/kg)
GFT$_1$; group administered Galgeuntang fermented with *Bifidobacterium breve* (7.5 ml/kg)
GFT$_2$; group administered Galgeuntang fermented with *Bifidobacterium breve* (15 ml/kg)
GFT$_3$; group administered Galgeuntang fermented with *Bifidobacterium breve* (30 ml/kg)
Statistical significances were calculated for the negative control (*p < 0.05, **p < 0.01).
$^a$Values are represented by mean.
$^b$±SD As described hereinbefore, the changes of body weight and liver weight were analyzed. As a result, it was confirmed that Galgeuntang and fermented Galgeuntang could be acting as an alleviator of inflammation in liver caused by the treatment of carbon tetrachloride.

Experimental Example 2

Histopathological Examination with Liver Tissues

In this example, histopathological examination was performed to investigate the effect of the experimental samples in the test animals induced with liver toxicity by the administration of carbon tetrachloride. The test animals were 30 male rats in total. Livers of the rats were fixed in 10% neutral formalin solution and then examined. Total 6 experimental groups including the normal control group were prepared as shown in Table 8.

TABLE 8

| Group | CCl$_4$ | Test material | Number of animal | Identification Number of animal |
|---|---|---|---|---|
| CON | X* | X | 5 | 1~5 |
| NCT | ○ | X | 5 | 6~10 |
| GGT | ○ | Galgeuntang | 5 | 11~15 |
| GFT$_1$ | ○ | Fermented Galgeuntang (low concentration) | 5 | 16~20 |
| GFT$_2$ | ○ | Fermented Galgeuntang (medium concentration) | 5 | 21~25 |
| GFT$_3$ | ○ | Fermented Galgeuntang (high concentration) | 5 | 26~30 |

Each test animal treated with carbon tetrachloride was evaluated by centrilobular necrosis, vacuolar degeneration, and inflammatory cells infiltration in liver cells. To compare the alleviation levels in experimental groups, average point was calculated for each group.

Figure 4:
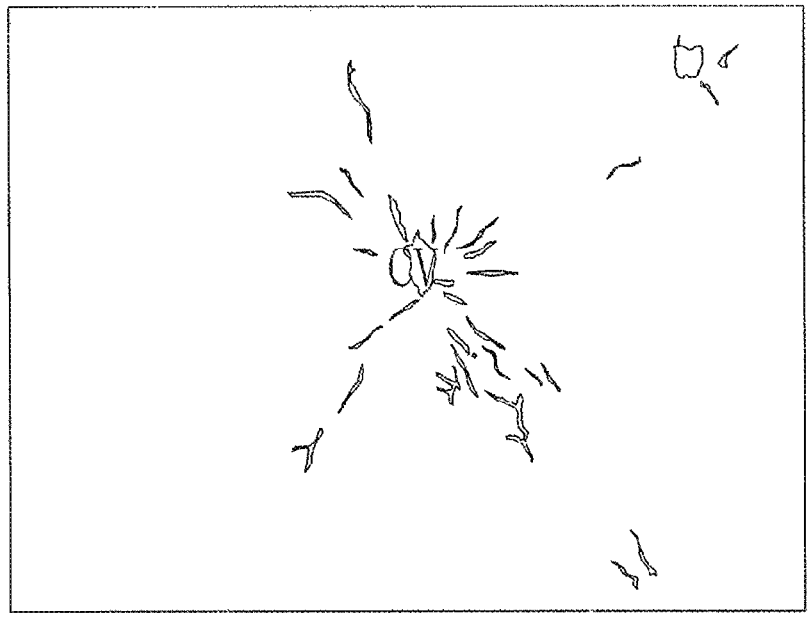
FIG. 4-FIG. 9 are depictions of photographs illustrating the results of histopathological examination on liver tissues performed in Experimental Example 2.
Figure 5:
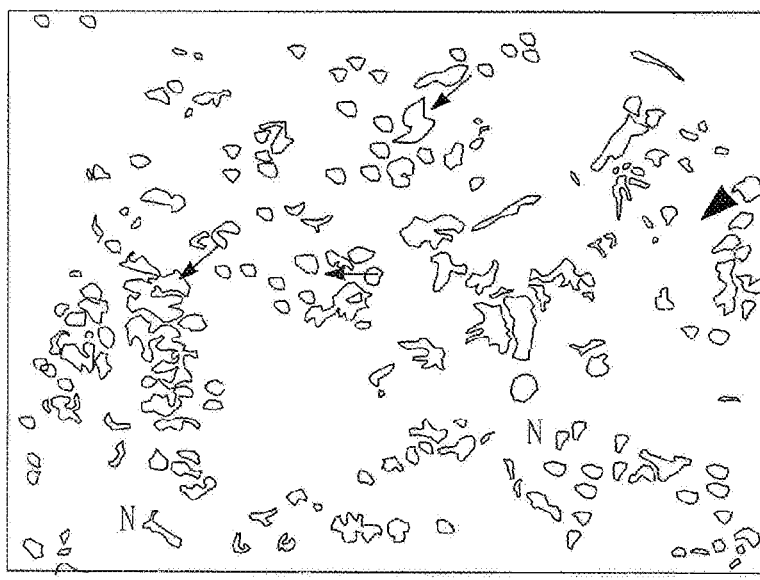

From the histopathological examination, no particular lesion was observed in the livers of all the animals of CON group (see FIG. 4), but various lesions induced by the treatment of carbon tetrachloride were observed in other groups. In NCT group, the degrees of centrilobular necrosis (N) and vacuolar degeneration (←) were even more significant, compared with other groups, and inflammatory cells infiltration (▲) was also observed (see FIG. 5).

Figure 6:
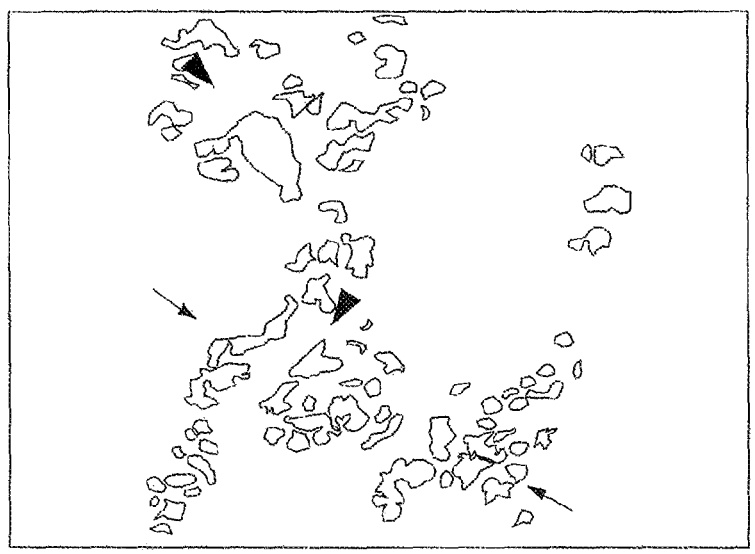
Figure 7:
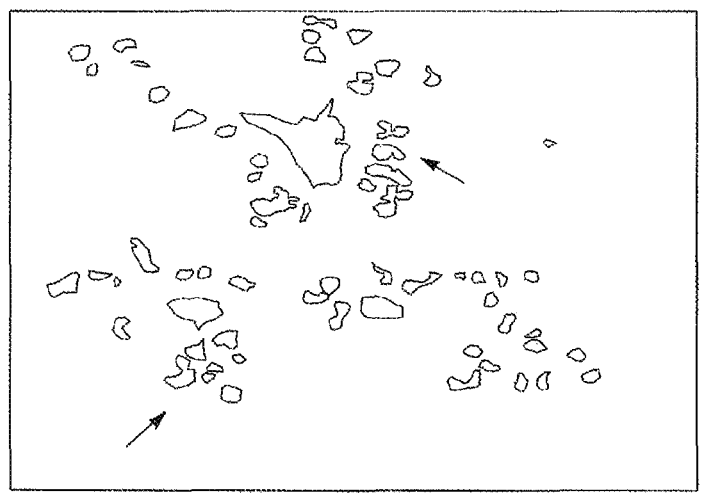
Figure 8:
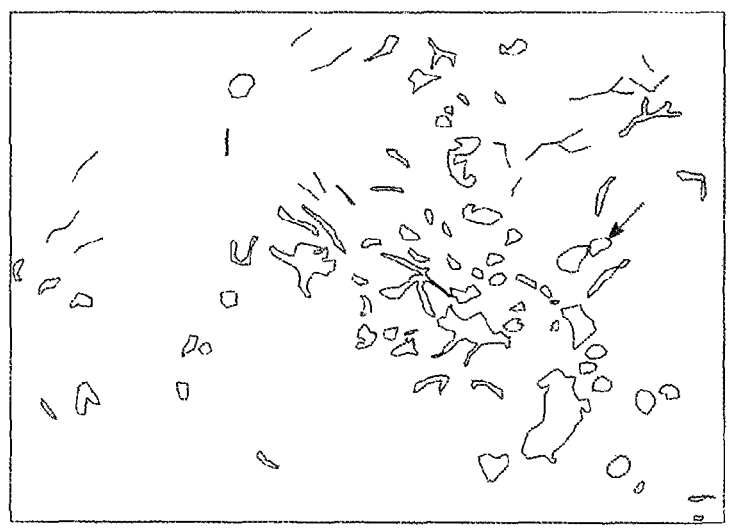
Figure 9:
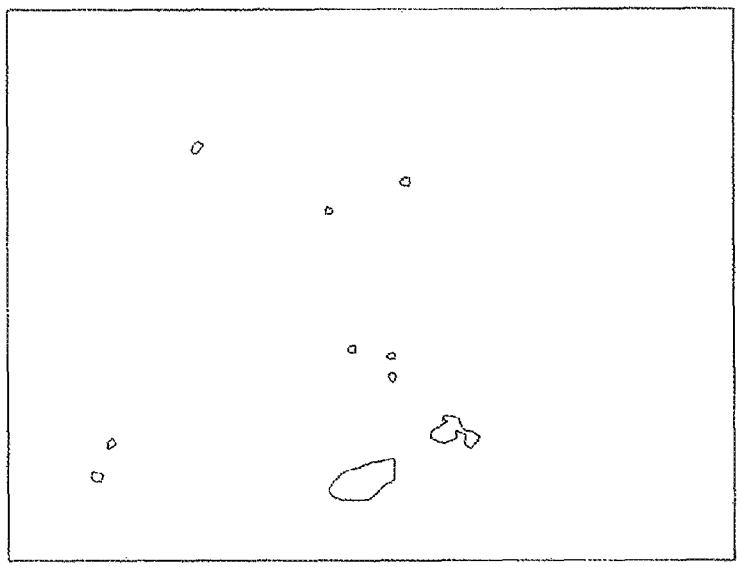

In the experimental groups treated with Galgeuntang (GGT, GFT$_1$, GFT$_2$ and GFT$_3$), centrilobular necrosis and vacuolar degeneration were not that significant, compared with NCT group, but inflammatory cells infiltration in GGT group was rather high. Lesion was reduced in GGT group and GFT$_1$ group similarly (see FIG. 6 and FIG. 7), and was less observed in GFT$_2$ group (see FIG. 8). Except one of inflammatory cells infiltration was medium, every observed lesions in GFT$_3$ group were minimum and minor, suggesting that GFT$_3$ group showed the biggest difference compared with NCT group (see FIG. 9).

Average point for each group calculated based on the results shown in FIG. 4 to FIG. 9 was presented in Table 9. In the calculation of the average point, the evaluation is presented as follows. +: minimum, ++: minor, +++: medium, ++++: severe.

TABLE 9

| | Severity rating | | |
|---|---|---|---|
| Group/Animal ID | centrilobular necrosis | vacuolar degeneration | inflammatory cells infiltration |
| CON 1, 2, 3, 4, 5 | −, −, −, −, − | −, −, −, −, − | −, −, −, −, − |
| Average point | 0/5 = 0 | 0/5 = 0 | 0/5 = 0 |
| NCT 6, 7, 8, 9, 10 | +, +, +++, +, +++ | +++, ++, ++++, ++, ++++ | ++, ++, ++, +, +++ |
| Average point | 9/5 = 1.8 | 15/5 = 3.0 | 10/5 = 2.0 |
| GGT(15 ml/kg) 11, 12, 13, 14, 15 | +, ++, +, ++, + | ++, +++, +++, ++, ++ | +++, +++, ++, ++, ++ |
| Average point | 7/5 = 1.4 | 12/5 = 2.4 | 12/5 = 2.4 |
| GFT$_1$(7.5 ml/kg) 16, 17, 18, 19, 20 | +, +, ++, ++, + | +++, +++, +, ++, ++ | +++, +, ++, +, +++ |

TABLE 9-continued

| Group/Animal ID | centrilobular necrosis | vacuolar degeneration | inflammatory cells infiltration |
|---|---|---|---|
| | | Severity rating | |
| Average point | 7/5 = 1.4 | 11/5 = 2.2 | 10/5 = 2.0 |
| $GFT_2$(15 ml/kg) 21, 22, 23, 24, 25 | +, +, −, +++, + | ++, ++, +, +++, ++ | +, ++, +, ++, ++ |
| Average point | 6/5 = 1.2 | 10/5 = 2.0 | 8/5 = 1.6 |
| $GFT_3$(30 ml/kg) 26, 27, 28, 29, 30 | +, +, +, +, + | +, ++, +, ++, + | +, +, ++, +, +++ |
| Average point | 5/5 = 1.0 | 7/5 = 1.4 | 8/5 = 1.6 |

To evaluate the effect of test materials on the damaged liver tissues of rats treated with carbon tetrachloride, histopathological examination was performed and the result of each group was compared.

As a result, in the experimental group treated with carbon tetrachloride, those histopathological changes known to be caused by carbon tetrachloride were observed[1)-3)]. Lesions caused by the treatment of carbon tetrachloride were mainly observed in liver cells around liver central vein (CV). In this example, vacuolar degeneration was more significant than necrosis. In NCT group, toxic lesion induced by carbon tetrachloride was different from each test animal, and thus it was almost impossible to compare the alleviation effect of such lesion among the test animals. So, lesion levels were all added together and produced as average point for each group, which could be used for the comparison of the overall alleviation effect.

As a result, the average point was increased in the following order: $CON<GFT_3<GFT_2<GFT_1<GGT<NCT$. The alleviation level of toxic lesions induced by carbon tetrachloride became higher as the dose of fermented Galgeuntang increased. The lesion was not completely eliminated even in the experimental group treated with high concentration of the test material and minor vacuolar degeneration was still observed in hepatic lobule cytoplasm. However, the lesion was least observed in the experimental group treated with high concentration of Galgeuntang. The inventors considered that it is important to execute additional experiment to evaluate whether the micro-vacuoles additionally observed in cytoplasm were attributed to a series of reaction according to the alleviation of lesion or attributed to another reaction caused by the treatment of high concentration of the test material.

In this example, infiltration of fibrin and inflammatory cells in liver serosa and liver cell necrosis were also observed among the animals treated with carbon tetrachloride. There has been no information given up to date about the effect of the administration of the test material on the said lesions, which makes accurate judgment difficult. It has only been presumed that intraperitoneal injection might somehow affect the lesions.

Based on the results obtained above, it was confirmed that the toxic lesion caused by carbon tetrachloride was most significant in NCT group, and the alleviation of the lesion resulted from the administration of the test material was most significant in $GFT_3$ group.

1) Hassan, N. S., Abbas, N. F., and Sharaf, H. A. (2003). Histopathological and histochemical studies on the taurine in preventing carbon tetrachloride-induced hepatic injury in the albino rat, Egypt. J. Hosp. Med., 10: 52-65.

2) Kim Hyoung-Chun, Park Eon-Sub, Yoo Jae-Hyung, and Song Kye-Yong (1989). Serochemical and Histopathological Observations on the Effect of Malotilate (Diisopropyl-1,3-dithiol-2-ylidene malonate) in Chronic Liver Injury Induced by Carbon Tetrachloride with or without Ethanol. The Korean Journal of Pathology, 23(2): 223-234.

3) Gopinath, C., Prentice, D. E., and Lewis, D. J. (2001). Atlas of experimental toxicological pathology (translated by Kang et al.). Chunggu Publishing Co., Ltd.

To screen the effect of Galgeuntang and fermented Galgeuntang on acute inflammation, SD rats were treated with carbon tetrachloride to cause acute hepatitis, followed by administrating Galgeuntang and fermented Galgeuntang (*Bifidobacterium breve*). Then, blood biochemical index was analyzed. As a result, the levels of AST, ALT, and LDH in serum were significantly reduced compared with the negative control. In particular, the effect of fermented Galgeuntang depends on dose. It was also confirmed that the test material reduced weight loss and increase of liver weight caused by carbon tetrachloride. When the test material was administered, the improving effect on centrilobular necrosis, vacuolar degeneration, and inflammatory cells infiltration was clearly confirmed. Therefore, it was confirmed that Galgeuntang has novel effect on relieving inflammation. And, the effect of fermented Galgeuntang on alleviating acute inflammation was higher as in vivo absorption rate of the fermented Galgeuntang was increased by bioconversion.

Preparation Example 1

Preparation of Pharmaceutical Composition

<1-1> Preparation of Soft Capsules

Soft capsules were prepared containing 100.0 mg of the lactic acid bacteria fermented Galgeuntang produced in Example 1, 175.0 mg of soybean oil, 45.0 mg of yellow beeswax, 127.5 mg of palm hardened oil, 21.0 mg of soybean phospholipid, 212.0 mg of gelatin, 50.0 mg of glycerin (specific gravity 1.24), 76.0 mg of D-sorbitol, 0.54 mg of paraoxymethylbenzoic acid, 0.90 mg of paraoxypropylbenzoic acid, 0.56 mg of methyl vanillin and a proper amount of yellow food color 203 per capsule according to the manufacturing process of soft capsule of the Korean Pharmacopoeia.

<1-2> Preparation of Tablets 100.0 mg of the lactic acid bacteria fermented Galgeuntang produced in Example 1, 90.0 mg of cornstarch, 175.0 mg of lactose, 15.0 mg of L-hydroxypropylcellulose, 5.0 mg of polyvinylpyrolidone 90 and a proper amount of ethanol were mixed homogeneously and granulized by wet-granulizing method. After adding 1.8 mg of magnesium stearate thereto, tableting was performed so that weight of a tablet can be 400 mg.

Preparation Example 2

Preparation of Health Food

<2-1> Preparation of Capsules 100.0 mg of the lactic acid bacteria fermented Galgeuntang produced in Example 1, 83.2 mg of cornstarch, 175.0 mg of lactose and 1.8 mg of magnesium stearate were mixed homogeneously. And then, capsules were prepared containing 360 mg of the mixture per capsule.

<2-2> Preparation of Beverage

Beverage was prepared to have the composition containing the lactic acid bacteria fermented Galgeuntang produced in Example 1 0.48-1.28 mg, honey 522 mg, thioctic acid amide 5 mg, nicotinic acid amide 10 mg, sodium riboflavin hydrochloric acid 3 mg, pyridoxine hydrochloride 2 mg, inositol 30 mg, orotic acid 50 mg, and water 200 ml.

<2-3> Preparation of Powders

Powders were prepared by mixing 2 g of the lactic acid bacteria fermented Galgeuntang produced in Example 1 and 1 g of lactose, which were filled in airtight packs according to the conventional method for preparing powders.

INDUSTRIAL APPLICABILITY

The composition of the present invention has treatment effect on liver toxicity, so that it can be effectively used as a liver function recovering agent or health food for liver function recovery.

We claim:

1. A method for prevention or treatment of liver toxicity comprising the steps of selecting a patient in need of prevention or treatment of liver toxicity, and administering a composition comprising lactic acid bacteria fermented Galgeuntang as an active ingredient to the patient, wherein the dose of the lactic acid bacteria fermented Galgeuntang is 15-40 ml per 1 kg/day for an adult, and wherein the composition reduces the activities of one or more enzymes selected from AST (aspartate aminotransferase), ALT (alanine aminotransferase), and LDH (lactate dehydrogenase), and the administration of the composition alleviates centrilobular necrosis, vacuolar degeneration, and inflammatory cell infiltration, wherein the Galgeuntang is prepared by hot water extraction of the mixture of medicinal herbs including 2-10 parts by weight of mahuang, 2-10 parts by weight of ginger, 2-10 parts by weight of jujube, 1-7 parts by weight of licorice, 1-7 parts by weight of peony, and 1-7 parts by weight of gyeji (*Cinnamomi ramulus*) with 12 parts by weight of Galgeun (*Puerariae radix*), and wherein the lactic acid bacteria are *Bifidobacterium breve*.

2. The method according to claim 1, wherein the lactic acid bacteria fermented Galgeuntang is prepared by fermenting the Galgeuntang inoculated with lactic acid bacteria.

3. The method according to claim 1, wherein the lactic acid bacteria fermented Galgeuntang is prepared by a method comprising the steps of:

preparing Galgeuntang by hot water extraction of a mixture of Galgeun (*Puerariae radix*), mahuang, ginger, jujube, licorice, peony and gyeji (*Cinnamomi ramulus*);

inoculating the prepared Galgeuntang with a culture solution of lactic acid bacteria mycelium; and inducing submerged fermentation of the inoculated Galgeuntang under anaerobic conditions to produce lactic acid bacteria fermented Galgeuntang.

4. The method according to claim 3, wherein the method further comprises the step of adjusting pH of Galgeuntang to 6~8 before inoculating the culture solution of lactic acid bacteria mycelium and after preparing Galgeuntang.

5. A method for recovery of liver function comprising the steps of selecting a patient in need of prevention or treatment of liver toxicity, and administering a health food comprising lactic acid bacteria fermented Galgeuntang as an active ingredient to the patient, wherein the dose of the lactic acid bacteria fermented Galgeuntang is 15-40 ml per 1 kg/day for an adult, and wherein the health food reduces the activities of one or more enzymes selected from AST (aspartate aminotransferase), ALT (alanine aminotransferase), and LDH (lactate dehydrogenase), and the administration of the health food alleviates centrilobular necrosis, vacuolar degeneration, and inflammatory cell infiltration, wherein the Galgeuntang is prepared by hot water extraction of the mixture of medicinal herbs including 2-10 parts by weight of mahuang, 2-10 parts by weight of ginger, 2-10 parts by weight of jujube, 1-7 parts by weight of licorice, 1-7 parts by weight of peony, and 1-7 parts by weight of gyeji (*Cinnamomi ramulus*) with 12 parts by weight of Galgeun (*Puerariae radix*), and wherein the lactic acid bacteria are *Bifidobacterium breve*.

6. The method according to claim 5, wherein the lactic acid bacteria fermented Galgeuntang is prepared by fermenting the Galgeuntang inoculated with lactic acid bacteria.

* * * * *